United States Patent [19]

Alferness et al.

[11] 4,066,086
[45] Jan. 3, 1978

[54] PROGRAMMABLE BODY STIMULATOR

[75] Inventors: Clifton A. Alferness, Woodinville, Wash.; John M. Adams, Anoka, Minn.

[73] Assignee: Medtronic, Inc., Minneapolis, Minn.

[21] Appl. No.: 722,626

[22] Filed: Sept. 13, 1976

Related U.S. Application Data

[63] Continuation of Ser. No. 584,131, June 5, 1975, abandoned.

[51] Int. Cl.² ............................................ A61N 1/36
[52] U.S. Cl. ............................ 128/421; 128/419 PG
[58] Field of Search ........... 128/419 C, 419 E, 419 P, 128/419 PG, 419 R, 420, 421, 422, 423

[56] References Cited

U.S. PATENT DOCUMENTS

| | | | |
|---|---|---|---|
| 3,195,540 | 7/1975 | Waller | 128/419 PG |
| 3,454,012 | 7/1969 | Raddi | 128/419 PG |
| 3,618,615 | 11/1971 | Greatbatch | 128/419 PG |
| 3,623,486 | 11/1971 | Berkovitz | 128/419 PG |
| 3,645,267 | 2/1972 | Hagfors | 128/421 |
| 3,662,758 | 5/1972 | Glover | 128/421 |
| 3,727,616 | 4/1973 | Lenzkes | 128/419 E |
| 3,774,619 | 11/1973 | Goldberg | 128/419 PG |
| 3,805,796 | 4/1974 | Terry, Jr. et al. | 128/419 PG |
| 3,833,005 | 9/1974 | Wingrove | 128/419 PG |
| 3,945,387 | 3/1976 | Adams | 128/419 PG |

Primary Examiner—William E. Kamm
Attorney, Agent, or Firm—Lindquist & Vennum

[57] ABSTRACT

A body implantable device for providing electrical stimulation to living animal tissue. The device includes a pulse generator having at least one alterable output parameter and circuitry responsive to first externally generated signals for altering the alterable output parameter in predetermined correspondence with the number of said first signals. The output parameter altering circuitry is enabled only during the occurrence of second signals having characteristics discriminable from the characteristics of the first signals. In a preferred embodiment, the first signals are pulses of radio frequency energy and the second signals are magnetic. The invention may be embodied in a cardiac pacemaker of either the asynchronous or demand type and the second signals may be employed to cause a demand cardiac pacemaker to revert to an asynchronous operation.

29 Claims, 2 Drawing Figures

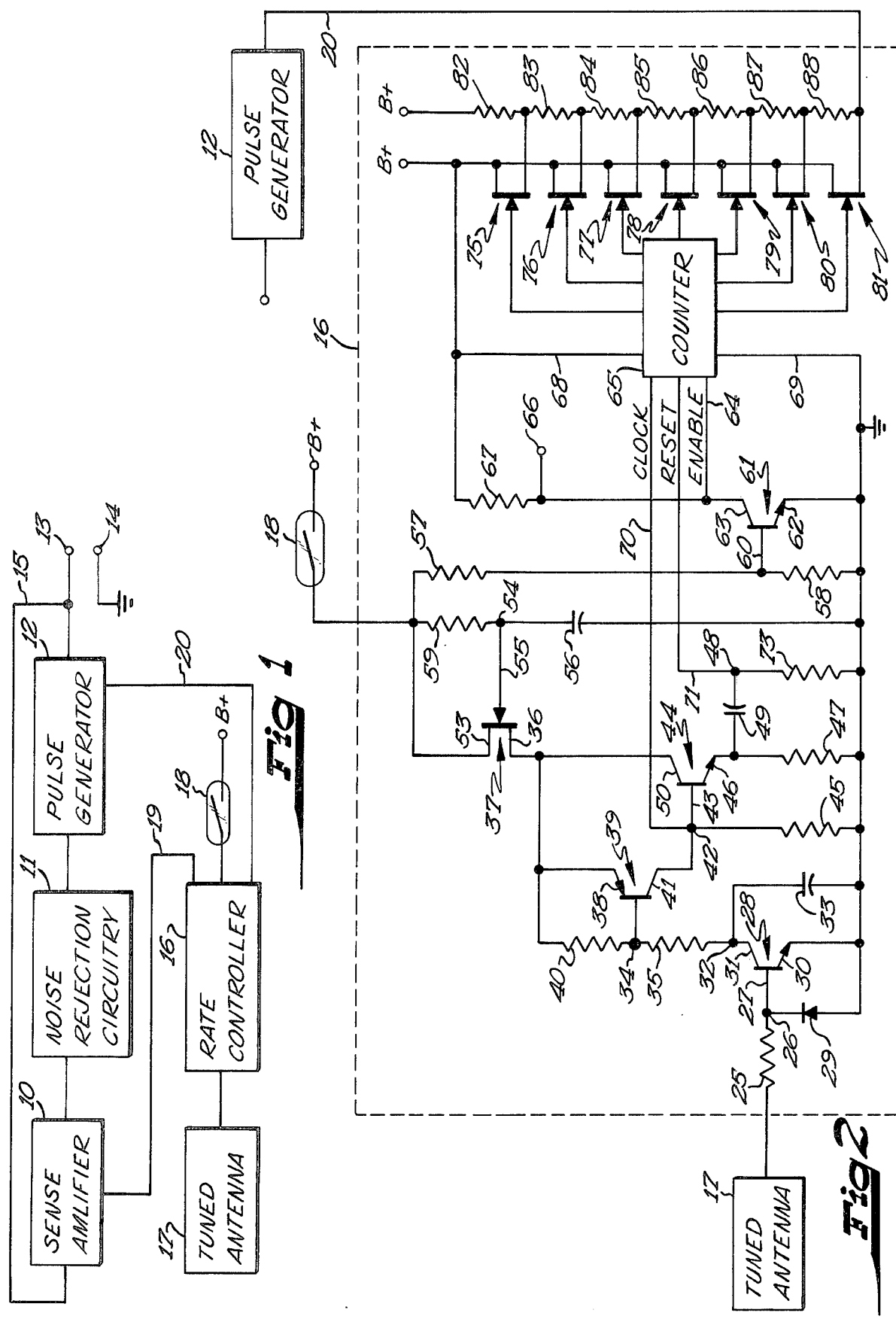

PROGRAMMABLE BODY STIMULATOR

This is a continuation of application Ser. No. 584,131, filed June 5, 1975, now abandoned.

BACKGROUND OF THE INVENTION

The output parameters of many prior art cardiac pacemakers are either preset during fabrication or established at the time of implant. With such pacemakers, adjustment of any output parameter requires a surgical exposure of the pacemaker itself. Other pacemakers are adjustable through the use of a needle-like tool.

More recently, various systems have been advanced for altering the output parameters of an implanted cardiac pacemaker with transmitted signals of electomagnetic energy. The pacemakers of these systems have included circuitry responsive to a preselected signal for altering at least one output parameter of the pacemaker on the occurrence of the signal. For example, in U.S. Pat. No. 3,311,111, the use of bistable magnetic reed switches is proposed for the control of pulse rate, voltage, current or duration as well as the selection of alternate output paths or leads. Other systems have been proposed in which pulse signals are used to advance a counter with the accumulated count in the counter serving to establish the value of the output parameter or parameters to be altered.

Both of the systems described above are susceptible to transient magnetic fields and/or electrical noise. Indeed, a variation of the "pulsed signal" system which reduces probability of output parameter alteration by extraneous noise is advanced in U.S. Pat. No. 3,805,796. In this system, a first counter advances in response to all detected signals while a second counter advances only in response to signals detected after the count of the first counter reaches a preselected value. The value of the count in the second counter is employed to control at least one alterable output parameter. Thus, extraneous signals which are incapable of advancing the first counter to the preselected value cannot result in an alteration of the pacemaker output parameters. However, signals which are capable of advancing the first counter have the inherent ability of advancing the second counter, subject only to their continued presence. Thus, while the system of U.S. Pat. No. 3,805,796 does reduce the probability that a detected extraneous signal will result in an alteration in the pacemaker's output parameters, it does not limit the extraneous signals that will be detected. In essence, this system limits its response to detected signals but, does not limit the signals which it will detect.

SUMMARY OF THE PRESENT INVENTION

The present invention provides a body implantable device for providing electrical stimulation to living animal tissue. At least one output parameter of the device may be altered by externally generated signals while the ability of the device to detect those signals is restricted. For example, the device may be an implanted cardiac pacemaker of the type having a pulse generator with at least one alterable output parameter and include circuitry responsive to first externally generated signals for altering the alterable output parameter in predetermined correspondence with the number of the first signals. Additional circuitry responsive to second externally generated signals, having characteristics discriminable from the characteristics of the first signals, is employed to enable the circuitry responsive to the first signals only during the occurrence of the second signals. In this manner, the presence of extraneous signals of the type capable of altering the output parameters of the pacemaker are prevented from doing so in the absence of the second signals. Thus, the present invention limits the ability of the implanted device to detect extraneous signals as opposed to a limitation on the response of the device to those signals. The present invention may be embodied in implanted body stimulators of all types in which the ability to alter an output parameter or parameters may be useful. When the implanted device is a demand cardiac pacemaker, the second signal may be employed to produce an automatic reversion to asynchronous or continuous operation.

While the major criterion of the first and second signals is that they each have predetermined characteristics discriminable from each other, it has been found advantageous to employ pulses of radio frequency energy for the first signals and a magnetic field as the second signal. Also, the ability of the device of the present invention to detect extraneous noise may be further limited by enabling the circuitry responsive to the first signals a predetermined time following initiation of one of the second signals.

BRIEF DESCRIPTION OF THE DRAWINGS

FIG. 1 illustrates the present invention embodied with a demand cardiac pacemaker.

FIG. 2 further illustrates a portion of the embodimental FIG. 1.

DETAILED DESCRIPTION OF THE DRAWINGS

FIG. 1 illustrates the operation of the present invention within a demand cardiac pacemaker. The pacemaker consists essentially of a sense amplifier 10, noise rejection circuitry 11, pulse generator 12 and terminals 13 and 14. The terminals 13 and 14 are adapted for connection to the body of a patient, in known manner, to apply cardiac stimulating pulses from the pulse generator 12 to the heart as well as to pick up signals representative of natural heart activity.

The pulse generator 12 is of the type having resetable timing circuitry, the timing circuitry being reset by an inhibit signal from the sense amplifier 10 passed by the noise rejection circuitry 11. A signal appearing across the terminals 13 and 14 will be passed to the sense amplifier 10 via the line 15 and will result in the generation of an inhibit signal by the sense amplifier 10. The noise rejection circuitry 11 may be a filter or other known device which blocks those inhibit signals from the pulse generator 12 which have predetermined characteristics such as that which results from extraneous noise, for example. Thus, if the heart is beating naturally at a rate faster than the timing cycle of the pulse generator 12, each heart beat will result in the generation of an inhibit signal by the sense amplifier 10 and a restarting of the timing cycle of the pulse generator 12. So long as the heart continues to beat naturally at such a rate, no cardiac stimulating pulses will be produced by the pulse generator 12. However, if the rate of the heart should become slower than the timing cycle of the pulse generator 12 or, alternatively, if the heart should "skip" one or more beats, no inhibit signal(s) will be generated by the sense amplifier 10 and cardiac stimulating pulse(s) will be generated by the pulse generator 12 at the end of its timing cycle. Thus, a demand cardiac pacemaker of the type described to this point can induce a single missing heartbeat or series of heartbeats dependent on the natural activity of the heart itself. Of course, demand cardiac pacemakers take several known forms and the discussion to this point is intended as introductory only for the purposes of a better understanding of the present invention.

The present invention, within the embodiment of a demand cardiac pacemaker as illustrated in FIG. 1, and in addition to the functional elements 10 – 15 which form the demand cardiac pacemaker itself, may be described as including a rate controller 16, tuned antenna 17, reed switch 18 and output lines 19 and 20. The output line 19 carries a signal to enable or disable the sense amplifier 10 while the output line 20 interconnects the timing circuitry of the pulse generator 12 with selectible timing elements within the rate controller 16. For example, if the pulse generator 12 is of the type having RC timing circuitry, the output line 20 may interconnect that timing circuitry with a series of resistances within the rate controller 16, the value of the resistance within the rate controller 16 being selectible to control the pulse repetition rate of the pulse generator 12.

The selection of the resistance value within the rate controller 16 which is interconnected with the timing circuitry of the pulse generator 12 is made in predetermined correspondence with the number of pulse signals received at the tuned antenna 17. For example, a single burst of radio frequency energy received at the tuned antenna 17 may correspond to a pulse repetition rate of 60 pulses per minute and result in an interconnection of a resistance value within the rate controller 16 and the timing circuitry of the pulse generator 12 to produce that repetition rate while two bursts sensed at the tuned antenna 17 may correspond with a pulse repetition rate of 65 pulses per minute and result in the interconnection of a different resistance value in the rate controller 16. Of course, the particular pulse repetition rates desired may vary according to the application as may the correspondence between the number of bursts received at the tuned antenna 17 and a particular repetition rate.

The antenna 17 is tuned, in known manner, to receive pulses or bursts of radio frequency energy on a predetermined carrier frequency, 175 KHz., for example. The limited response of such antennas to particular frequency ranges is well known in the art and serves to restrict the response of the unit to extraneous noise. The rate controller of the present invention is further restricted from responding to extraneous noise by maintaining it in a disabled state except during the presence of a magnetic field, which field operates on reed switch 18 to enable the rate controller 16 to respond to pulse signals sensed at the tuned antenna 17. Thus, an alteration of the repetition rate of pulse generator 12 not only requires the presence of a signal which can be detected at the tuned antenna 17 but also requires the presence of a distinct signal capable of enabling the response of the rate controller. Thus, by rendering the rate controller 16 operative only during the application of concurrent discriminable signals the likelihood of an alteration of pulse repetition rate as a result of extraneous noise is greatly reduced.

Referring now to FIG. 2, here is shown the pulse generator 12, tuned antenna 17, reed switch 18 and their interconnection with circuitry forming a preferred embodiment of the rate controller 16. The antenna 17 is connected via resistor 25 to a junction 26. The junction 26 is connected to the base electrode 27 of a transistor 28 and to ground by a diode 29. The emitter electrode 30 of transistor 28 is connected to ground and its collector electrode 31 is connected to a junction 32. The junction 32 is connected to ground through a capacitor 33 and to a junction 34 by a resistor 35. The junction 34 is connected to the source electrode 36 of a field effect transistor 37 through resistor 40, to the base electrode of a transistor 39 and, through a resistor 40 to the emitter electrode 38 of the transistor 39. The collector electrode 41 of transistor 39 is connected to a junction 42, the junction 42 being connected to the base electrode 43 of a transistor 44 and to ground through a resistor 45. The emitter electrode 46 of transistor 44 is connected to ground through a resistor 47 and to a junction 48 through a capacitor 49. The collector electrode 50 of transistor 44 is connected to the source electrode 36 of field effect transistor 37.

The reed switch 18 connects a source of positive voltage, such as batteries, to the drain electrode 53 of field effect transistor 37 and, through a resistor 59, to a junction 54. The junction 54 is connected to the gate electrode 55 of field effect transistor 37 and to ground through a capacitor 56. The reed switch 18 also connected to ground through resistances 57 and 58 while the base electrode 60 of transistor 61 is interconnected between the resistances 57 and 58 with its emitter electrode 62 connected to ground. The collector electrode 63 of transistor 61 is connected to an enable input line 64 of a counter 65, to a terminal 66 and, through a resistor 67, to a source of positive voltage, such as batteries connected to B+ and ground. Lines 68 and 69 interconnect the counter 65 to the power source while a line 70 interconnects the clock input line of the counter 65 with the junction 42 and a line 71 interconnects the reset input of counter 65 with the junction 48.

The counter 65 has its first seven output states connected to the gate electrode of one of the field effect transistors 75-81. The drain electrodes of field effect transistors 75-81 are connected to a positive power supply while their source electrodes are connected between different series connected resistances 82-88. The resistance network of resistors 82-88 serially connect a positive power supply to the line 20 (see FIG. 1).

The counter 65 is of the type that will advance its state in response to each pulse appearing on its clock input line 70 following enablement of the counter by a signal appearing and remaining on its enable input line 64. Also, the counter 65 will be reset to its lowest state in response to a signal appearing on its reset input line 71 during its enablement by a signal appearing on the enable input line 64. Thus, assuming an enable signal appearing on the enable input line 64, a reset signal appearing on reset input line 71 will cause the counter 65 to apply a signal to the gate electrode of field effect transistor 75 and turn on that field effect transistor to effectively eliminate the resistance 82 from the serial resistance network between the positive power supply and the line 20. Assuming a subsequent clock pulse appearing on the clock input line 70, the counter 65 will advance its state and apply its output to the base electrode of field effect transistor 76 causing a turn on of FET 76 and the effective elimination of the resistances 82 and 83 from the serial resistance network between the power supply and the line 20. Subsequent clock pulses will result in further advances of the state of the counter 65 and effective sequential elimination of additional resistances in the serial resistance network of resistors 82 – 88. Thus, the number of clock pulses appearing on the clock input line 70 results in a selection of the overall resistance connected between the power supply and the line 20 and thus the resistance interconnected to the timing circuitry of the pulse generator 12 via the line 20. The pulse generator 12 may be constructed so as to increase its rate with decreasing resistance values connected between the power supply and the line 20. Of course, the value of the resistors 82–88 may be selected to provide any desired pulse generator repetition rate with the resistors 82 being operative only when the counter 65 has advanced its state beyond the output which will be applied to turn on the field effect transistor 81. For example, in the embodiment illustrated, there are seven field effect transistors 75–81. Thus, as the counter 65 advances through its first seven states there is a corresponding increase in the repetition rate of the pulse generator 12. However, assuming that the counter has more than seven states, when the counter advances past its seventh state all of the field effect transistors 75–81 will be non-conductive and all of the resistance 82–88 will conduct and produce the lowest repetition rate in the pulse generator 12. Of course, the resistance 82 can be eliminated such that the lowest repetition rate of pulse generator 12 will result when the field effect transistor 75 is conductive (i.e., when the counter is in its lowest state). However, it may be desirable to provide a relatively low repetition rate for selection while reducing the probability of an accidental selection of that rate. For example, it is generally regarded that a heart beat of approximately 40 beats per minute is the lowest heartbeat capable of sustaning life. It may be desireable to select a repetition rate lower than 40 beats per minute for a limited period of time to monitor natural heart activity while having the capability of inducing heart activity at the lower rate. Thus, the overall resistance of resistors 82–88 may be selected to provide a pulse generator repetition rate of 30 beats per minute while the arrangement illustrated in FIG. 2 prevents the selection of that rate except by advancing the counter 65 past its seventh state. The initial seven states may correspond to pulse generator repetition rates of 60, 65, 70, 75, 80, 90, and 100 pulses per minute, respectively.

The reed switch 18 is normally open and, when open, the rate controller 16 is disabled and is unable to respond to signals received by the tuned antenna 17. When the reed switch 18 is closed, as by placing it in a magnetic field, the capacitor 33 beings to charge to B+ through the resistances 35 and 40 and the field effect transistor 37. However, the voltage of the source electrode 36 of field effect transistor 37 cannot build faster than the charge on capacitor 56 which charges through resistor 59. Thus, resistor 59 and capacitor 56 provide a delay between the closing of the reed switch 18 and full charging of the capacitor 33. When the capacitor 33 is fully charged, the signal appearing on the base electrode 27 of the transistor 28 will turn on the transistor 28 and discharge the capacitor 33. As capacitor 33 discharges, transistor 39 turns on to apply a signal to the junction 42. The signals applied to the junction 42 are demodulated signals of the radio frequency signals received at antenna 17. The signals appearing at the junction 42 are applied to the counter 65 as clock pulses via the clock implse imput 70 and then serve as control pulses for the counter 65.

In addition to being applied to the counter 65 as a clock pulse, the signals appearing at the junction 42 are applied to the base electrode 43 of transistor 44 causing that transistor to turn on during the occurrence of each signal at the junction 42. The capacitor 49 will charge through resistor 73 during the on time of transistor 44 creating a spike at junction 48 which is applied as a reset signal to the counter 65 via reset input line 71.

The capacitor 49 discharges through resistances 47 and 73 when the transistor 44 is off. However, resistor 47 is selected to be very large relative to resistor 73 such that capacitor 49 will discharge relatively slowly and spikes subsequent to the initial spike resulting from the first turn on of transistor 44 will be below the threshold level of the counter 65 and will not be sensed as a reset signal. Also, inasmuch as the reset signal results from the charging of the capacitor 49, a reset signal resulting from the first demodulated signal appearing at the junction of 42 will be applied to the counter 65 after the clock pulse from that signal is applied assuring that the first pulse input signal to the rate controller 16 result in a resetting of the counter 65 to its lowest state and a turn on of the field effect transistor 75.

In addition to the above, closing of the reed switch 18 causes the transistor 61 to turn on and enable the counter 65 during the time that the reed switch 18 remains closed. Additionally, the enable signal resulting from the turn on of the transistor 61 is applied to the terminal 66. The terminal 66 may be connected to the line 19 (see FIG. 1) to disable the sense amplifier of a demand cardiac pacemaker during the time that the reed switch 18 remains closed. In essence, with the terminal 66 connected to the line 19, closing of the reed switch 18 causes a reversion of the demand cardiac pacemaker to a continuous or asynchronous mode of operation. Sense amplifiers suitable for use as a sense amplifier 10 illustrated in FIG. 1 having an enable/disable input are known to the prior art.

From the above, it is apparent that the present invention provides a device capable of selectively altering the alterable output parameters of implantable body stimulators. The device is suitable for use with cardiac pacemakers of any known type and may be similarly embodied within other known body stimulators. Additionally, while the device has been discussed with reference to an alteration of the repetition rate, its output may be similarly employed for the control of pulse power level as by amplitude or duration control as well as the selection of alternate output paths or leads or all of the above. However, it is contemplated that within the context of a pacemaker, the parameter which is most often desirable to control is its repetition rate. Within that context, it has been found advantageous to construct the rate controller disclosed in FIG. 2 with the following values or part designations:

| Resistors | Ohms |
| --- | --- |
| 25, 35, 40, 73 | 100K |
| 45, 67 | 2M |
| 47, 59 | 20M |
| 57, 58 | 10M |
| 82 | 5.01M |
| 83 | 388K |
| 84 | 332K |
| 85 | 387K |
| 86 | 352K |
| 87 | 417K |
| 88 | 337K |
| Capacitors | Microfarads |
| 33 | 0.001 |
| 49 | 0.001 |
| 56 | 0.047 |
| PNP Transistors | 2N3799 DICE |
| NPN Transistors | 2N2484 DICE |
| Field Effect Transistors | Similar to 2N4338 DICE except $V_p$ shall be in |

| Resistors | Ohms |
|---|---|
| | the range −0.2 to −1.0 volts at $I_D$ = 10nA and $V_{DS}$ = 5V. |
| Counter 65 | National Semiconductor Part No. MM4617A DICE |
| Diode 29 | 1N4531 DICE |

It is to be understood that, within the scope of the appended claims, the invention may be practical otherwise than as specifically described.

What is claimed is:

1. In a body-implantable device for providing electrical stimulation to living animal tissue of the type having pulse generator means with at least one alterable output parameter, output means adapted for connection to said tissue and means responsive to externally generated signals for programming said alterable output parameter in predetermined correspondence with said signals, the improvement wherein said programming means comprises:

means for detecting first externally generated signals of predetermined characteristics;

means responsive to detected first signals for altering said alterable output parameter in predetermined correspondence with said first signals;

means for detecting second externally generated signals of predetermined characteristics discriminable from the characteristics of said first signals; and means responsive to detected second signals for enabling said output parameter altering means only during the occurrence of said second signals.

2. The device of claim 1 wherein said enabling means enables said output parameter altering means a predetermined time following the initiation of one of said second signals.

3. The device of claim 1 wherein said output parameter altering means comprises means for generating a control signal on the occurrence of each of said first signals and means responsive to said control signals for altering said output parameter in predetermined correspondence with the number of said control signals, said enabling means comprising means for allowing the generation of a control signal only during the occurrence of said second signals.

4. The device of claim 3 wherein said enabling means further comprises means for preventing the generation of a control signal for a predetermined time following the intitiation of one of said second signals.

5. The device of claim 3 wherein said control signal responsive means includes counter means having a plurality of sequential states for advancing its state in response to each control signal and further comprising means for resetting said counter means to a preselected state in response to the first control signal following the initiation of one of said second signals.

6. The device of claim 5 wherein said enabling means further comprises means for preventing the generation of a control signal for a predetermined time following the initiation of one of said second signals.

7. The device of claim 6 wherein said resetting means resets said counter means to said preselected state after said counter has advanced its state in response to the first control signal following the initiation of one of said second signals.

8. The device of claim 6 wherein said enabling means comprises means for enabling said counter means only during the occurrence of said second signals.

9. The device of claim 1 wherein said output parameter altering means includes counter means having a plurality of sequential states for advancing its state in response to said first signals, said enabling means comprising means for enabling said counter means only during the occurrence of said second signals.

10. The device of claim 1 wherein said first signals are pulsed $rf$ signals and said second signals are magnetic.

11. The device of claim 1 wherein said device comprises a cardiac pacemaker, said output means being adapted for connection to the heart.

12. The device of claim 11 further comprising means adapted for connection to the heart to sense heart activity including means for inhibiting said pulse generator when the sensed activity satisfies certain preselected parameters, said enabling means including means for disabling said inhibiting means during the occurrence of said second signals.

13. The device of claim 12 wherein said enabling means enables said output parameter altering means a predetermined time following the initiation of one of said second signals.

14. The device of claim 12 wherein said output parameter altering means comprises means for generating a control signal on the occurrance of each of said first signals and means responsive to said control signals for altering said output parameter in predetermined correspondence with the number of said control signals, said enabling means comprising means for allowing the generation of a control signal only during the occurrence of said second signals.

15. The device of claim 14 wherein said enabling means further comprises means for preventing the generation of a control signal for a predetermined time following the initiation of one of said second signals.

16. The device of claim 14 wherein said control signal responsive means includes counter means having a plurality of sequential states for advancing its state in response to each control signal and further comprising means for resetting said counter means to a preselected state in response to the first control signal following the initiation of one of said second signals.

17. The device of claim 16 wherein said enabling means further comprises means for preventing the generation of a control signal for a predetermined time following the initiation of one of said second signals.

18. The device of claim 17 wherein said resetting means resets said counter means to said preselected state after said counter means has advanced its state in response to the first control signal following the initiation of one of said second signals.

19. The device of claim 17 wherein said enabling means comprises means for enabling said counter means only during the occurrence of said second signals.

20. The device of claim 12 wherein said output parameter altering means includes counter means having a plurality of sequential states for advancing its state in response to said first signals, said enabling means comprising means for enabling said counter means only during the occurrence of said second signals.

21. The device of claim 12 wherein said first signals are pulsed $rf$ signals and said second signals are magnetic.

22. The device of claim 11 wherein said first signals are pulsed *rf* signals and said second signals are magnetic.

23. In a body-implantable device for providing electrical stimulation to living animal tissue of the type having pulse generator means with at least one alterable output parameter, output means adapted for connection to said tissue and means responsive to externally generated signals for programming said output parameter in predetermined correspondence with said signals, the improvement wherein said programming means comprises:
  means for detecting first externally generated signals of predetermined characteristics;
  means responsive to detected first signals for generating a sequence of control signals, one control signal on the occurrence of each of said first signals;
  counter means having a plurality of sequential states and connected to receive said control signals for advancing its state in response to each control signal;
  means responsive to said control signals for resetting said counter means in response to the first control signal in a sequence of control signals;
  means for detecting second externally generated signals of predetermined characteristics discriminable from the characteristics of said first signals; and
  means responsive to detected second signals for enabling said control signal generating means only during the occurrence of said second signals.

24. The device of claim 23 wherein said control signal generating means comprises means responsive to transmitted pulses of radio frequency energy and means for demodulating said radio frequency energy pulses.

25. The device of claim 24 wherein said enabling means comprises magnetically operable switch means for selectively enabling said demodulating means.

26. The device of claim 25 further comprising means interconnecting said magnetically operable switch means and said demodulating means for delaying the enabling of said demodulating means by a predetermined time interval.

27. The device of claim 26 wherein said delaying means comprises:
  transistor switch means interconnecting said magnetically operable switch means and said demodulating means and responsive to said magnetically operable switch means for enabling said demodulating means; and
  circuit means for delaying the enabling response of said transistor switch means to said magnetically operable switch means for a predetermined time interval.

28. The device of claim 27 further comprising means interconnecting said counter means and said magnetically operable switch means and responsive to said magnetically operable switch means for selectively enabling said counter means.

29. The device of claim 28 wherein said resetting means comprises energy storage means and means enabled by said enabling means for charging said energy storage means on the occurrence of each control signal.

* * * * *

REEXAMINATION CERTIFICATE (204th)
United States Patent [19]
Alferness et al.

[11] B1 4,066,086
[45] Certificate Issued Jun. 5, 1984

[54] PROGRAMMABLE BODY STIMULATOR

[75] Inventors: Clifton A. Alferness, Woodinville, Wash.; John M. Adams, Anoka, Minn.

[73] Assignee: Medtronic, Inc., Minneapolis, Minn.

Reexamination Request:
No. 90/000,402, Jun. 13, 1983

Reexamination Certificate for:
Patent No.: 4,066,086
Issued: Jan. 3, 1978
Appl. No.: 722,626
Filed: Sep. 13, 1976

Related U.S. Application Data

[63] Continuation of Ser. No. 584,131, Jun. 5, 1973, abandoned.

[51] Int. Cl.³ .............................................. A61N 1/36
[52] U.S. Cl. ............................ 128/421; 128/419 PG
[58] Field of Search ........ 129/419 C, 419 E, 419 PG, 129/419 PS, 419 PT, 419 R, 421, 422, 423

[56] References Cited
U.S. PATENT DOCUMENTS

| | | | |
|---|---|---|---|
| 3,311,111 | 3/1967 | Bowers | 128/422 |
| 3,631,860 | 1/1972 | Lopin | 128/419 PG |
| 3,805,796 | 4/1974 | Terry, Jr. et al. | 128/419 PG |

FOREIGN PATENT DOCUMENTS

| | | |
|---|---|---|
| 985797 | 3/1965 | United Kingdom |
| 1108858 | 4/1968 | United Kingdom |
| 1394412 | 5/1972 | United Kingdom |

OTHER PUBLICATIONS

"An Implantable Pacemaker for the Reduction of Heart Rate", Richard S. C. Cobbold, et al., Med. Electron. Biol. Engng. vol. 3, pp. 273-278, Pergamon Press, 1965.
"Cardiac Sentinel" Information Sheet, alleged publication date 1961, 2 pages.
Litus, Jr., "RCA Application Note ICAN 6498", 10/70, pp. 1-6.
Medtronic publication TC 68152, Sep. 1968, pp. 1-20.

*Primary Examiner*—William E. Kamm

[57] ABSTRACT

A body implantable device for providing electrical stimulation to living animal tissue. The device includes a pulse generator having at least one alterable output parameter and circuitry responsive to first externally generated signals for altering the alterable output parameter in predetermined correspondence with the number of said first signals. The output parameter altering circuitry is enabled only during the occurrence of second signals having characteristics discriminable from the characteristics of the first signals. In a preferred embodiment, the first signals are pulses of radio frequency energy and the second signals are magnetic. The invention may be embodied in a cardiac pacemaker of either the asynchronous or demand type and the second signals may be employed to cause a demand cardiac pacemaker to revert to an asynchronous operation.

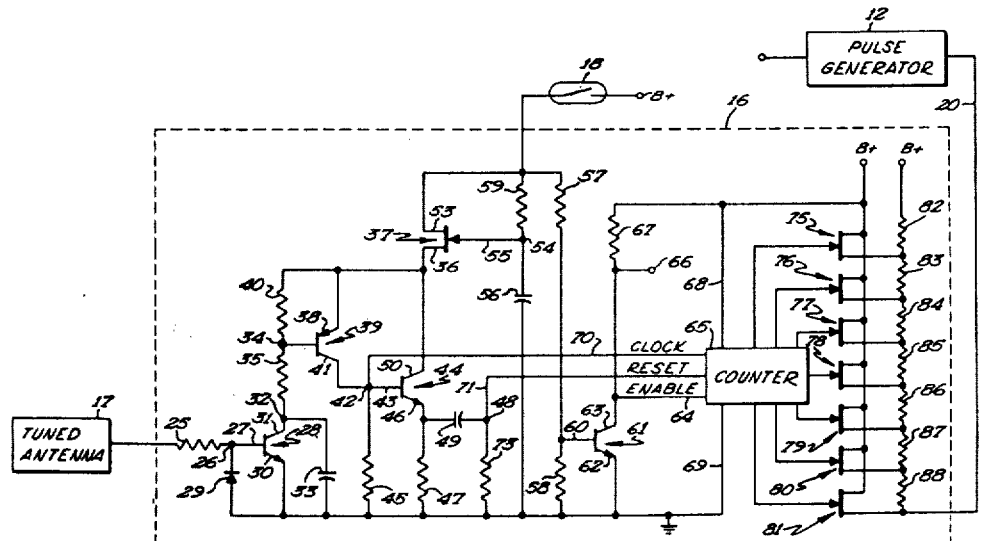

REEXAMINATION CERTIFICATE ISSUED UNDER 35 U.S.C. 307.

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 10 and 23 are determined to be patentable as amended:

Claims 2-9, 11-22, and 24-29, dependent on amended claims, are determined to be patentable.

New claims 30-31 are added and determined to be patentable.

1. In a body-implantable device for providing electrical stimulation *pulses* to living animal tissue of the type having pulse generator means with at least one alterable output parameter, output means adapted for connection to said tissue, and *programming* means responsive to *first* externally generated signals for programming said alterable output parameter in predetermined correspondence with *the parameter programming content of* said *first* signals, *in such a manner that upon cessation of said first signals, the output parameter will remain at the value to which it has been altered, until reprogrammed*[, the improvement wherein said programming means comprises:]*;*
   receiving means for detecting *said* first externally generated signals of predetermined characteristics;
   *parameter altering* means responsive to *said* detected first signals for altering said alterable output parameter in predetermined correspondence with *said parameter programming content of* said first signals *which after said altering operates with said altered parameter until said parameter is reprogrammed to another value; the improvement comprising:* [;]
   detection means for detecting second externally generated *magnetic field* signals *which is actuated upon said detection of said second signals, said second signals being* of predetermined characteristics *which are* discriminable from the characteristics of said first signals *by said detection means, so that said detection means is not actuated by said first signals, and by said receiving means so that said receiving means will not detect parameter programming content in said second signals*; and,
   means responsive to *the actuation of said detection means by said* detected second signals for *energizing said receiving means and* enabling said output parameter altering means *to be responsive to said first signals* only during the occurrence of said second signals.

10. The device of claim 1 wherein said first signals are pulsed rf signals and said second signals are *permanent* magnetic *field* signals *and said detection means comprise a normally-open magnetic reed-switch that closes upon detection of said permanent magnetic field signals, and* which upon said closure couples a D.C. voltage to said *receiving means.*

23. In a body-implantable device for providing electrical stimulation *pulses* to living animal tissue of the type having pulse generator means with at least one alterable output parameter, output means adapted for connection to said tissue, and *programming* means responsive to *first* externally generated signals for programming said *alterable* output parameter in predetermined correspondence with *the parameter programming content of* said *first* signals [the improvement wherein said programming means comprises:] *in such a manner that upon cessation of said first signals, the output parameter will remain at the value to which it has been altered, until reprogrammed*[,]*;*
   receiving means for detecting *said* first externally generated signals of predetermined characteristics;
   *control signal generating* means responsive to detected first signals for generating a sequence of control signals, one control signal on the occurrence of each of said first signals;
   counter means having a plurality of sequential states and connected to receive said control signals for advancing its state in response to each control signal; *and,*
   means responsive to said control signals for resetting said counter means in response to the first control signals in a sequence of control signals; *the improvement comprising:*
   *detection* means for detecting second externally generated *magnetic field* signals *which is actuated upon said detection of said second signals, said second signals being* of predetermined characteristics *which are* discriminable from the characteristics of said first signals *by said detection means, so that said detection means is not actuated by said first signals, and by said receiving means so that said receiving means will not detect parameter programming content in said second signals*; and,
   means responsive to *the actuation of said detection means by said* detected second signals *for energizing said receiving means and* enabling said control signal generating means *to be responsive to said first signals* only during the occurrence of said second signals.

*30. In a body implantable cardiac pacing device for providing electrical cardiac stimulation pulses to a patient in which said device is implanted comprising:*
   *a pulse generator for producing said stimulation pulses;*
   *output means coupled to receive said stimulation pulses and to supply them to said patient;*
   *an antenna coupled to receive externally transmitted electrical signals representative of programming information;*
   *output stimulation pulse altering means comprising receiving means in communication with said antenna for receiving said transmitted electrical signals and for providing digital signals representative of said programming information;*
   *storage and control means for receiving said digital signals, and for storing said program information and for controlling said pulse generator in accordance with said programming information so that at least one alterable parameter of the stimulation pulses that are produced by said pulse generator continually corresponds with the programming information that was previously stored in said storage and control means until such time that additional electrical signals con-* taining new programming information are transmitted; and, an electrical power source for supplying energization to said receiving means, the improvement comprising:

a normally open magnetically-operated switch means which is closed by the application by an external control magnetic field, when the programming of at least one alterable parameter of said output pulses is desired and opened by the removal of said control magnetic field upon the completion of the desired reprogramming, and which when closed, couples said power source to said receiving means wherein:

said receiving means is constructed so that it is capable of translating said received electrical signals into said digital signals only during the time that both said external control magnetic field is coupled so as to close said magnetically-operated switch and said external electrical transmitted signals representative of programming information are coupled to said antenna; and, said storage and control means is effective in controlling said pulse generator to respond to the new programming information that was received when said magnetically-actuated switch means was closed after said control magnetic field is removed and said magnetically-actuated switch means is correspondingly opened again; and, said receiving means is further constructed so that it is not capable of translating the opening and closing of said magnetically-operated switch means into said digital signals when said opening and closing is the result of extraneous non-control magnetic fields that the patient may encounter.

31. In a body implantable cardiac pacing device as claimed in claim 30 wherein:

said device comprises sensing and inhibiting means constructed so as to sense natural heart activity and to temporarily inhibit the production of output pulses by said pulse generator in response thereto the further improvement wherein:

said magnetically-actuated switch means is coupled to said sensing and inhibiting means and said sensing and inhibiting means is constructed so that it is capable of inhibiting the production of output pulses by said pulse generator when said magnetically-actuated switch means is open, but is not capable of inhibiting said output pulses from said pulse generator when said magnetically-actuated switch means is closed due to the presence of said control magnetic field.

* * * * *